United States Patent [19]

Sakuma et al.

[11] Patent Number: 4,939,925
[45] Date of Patent: Jul. 10, 1990

[54] METHOD OF PERFORMING MEASUREMENT OF HEMATOCRIT VALUE AND SEPARATE SAMPLING OF BLOOD COMPONENT

[75] Inventors: Hajime Sakuma, Hachioji; Toshiyuki Sasaki, Fussa; Katsumi Komatsu, Tokyo, all of Japan

[73] Assignee: Olympus Optical Co., Ltd., Tokyo, Japan

[21] Appl. No.: 323,568

[22] Filed: Mar. 13, 1989

[30] Foreign Application Priority Data

Mar. 23, 1988 [JP] Japan .................................. 63-68739

[51] Int. Cl.$^5$ ............................................ G01N 33/49
[52] U.S. Cl. ..................................... 73/61.4; 73/863.02
[58] Field of Search ............ 73/864,81, 864.85, 863.01, 73/863.02, 61.4

[56] References Cited

U.S. PATENT DOCUMENTS

| | | | |
|---|---|---|---|
| 3,754,444 | 8/1973 | Ure et al. | 73/863,01 |
| 4,028,930 | 6/1977 | Moreno | 73/61.4 |
| 4,219,440 | 8/1980 | Runck et al. | 356/39 X |
| 4,487,830 | 12/1984 | Takaganagi et al. | 73/863.01 X |
| 4,577,514 | 3/1986 | Bradley et al. | 73/863.01 |
| 4,829,837 | 5/1989 | Telfer | 73/863.01 |
| 4,848,900 | 7/1989 | Kuo et al. | 73/61.4 X |

FOREIGN PATENT DOCUMENTS

| | | |
|---|---|---|
| 55-31989 | 3/1980 | Japan . |
| 57-50659 | 3/1982 | Japan . |
| 60-93348 | 5/1985 | Japan . |
| 62-269037 | 11/1987 | Japan . |

*Primary Examiner*—Tom Noland
*Attorney, Agent, or Firm*—Frishauf, Holtz, Goodman & Woodward

[57] ABSTRACT

A method of performing measurement of a hematocrit value and separate sampling of plasma and blood cells, simultaneously. A probe including a pair of detection electrodes each in the form of a suction nozzle, is lowered from a certain initial height into a sample vessel containing blood that has bveen separated into an upper plasma layer and a lower blood cell layer, while the probe travel distance is monitored. When the detection electrodes touch the surface of the plasma layer, the plasma is sampled into a corresponding sampling vessel through one of the electrode suction nozzles. The probe is then lowered further until the electrodes touch the surface of the blood cell layer, and the blood cells are sampled into a different sampling vessel through the other one of the suction nozzles. A total sample blood volume and the volume of the blood cells are calculated in accordance with the measured travel of the probe between the upper and lower layers, and a hematocrit value is determined from the calculated volumes.

7 Claims, 2 Drawing Sheets

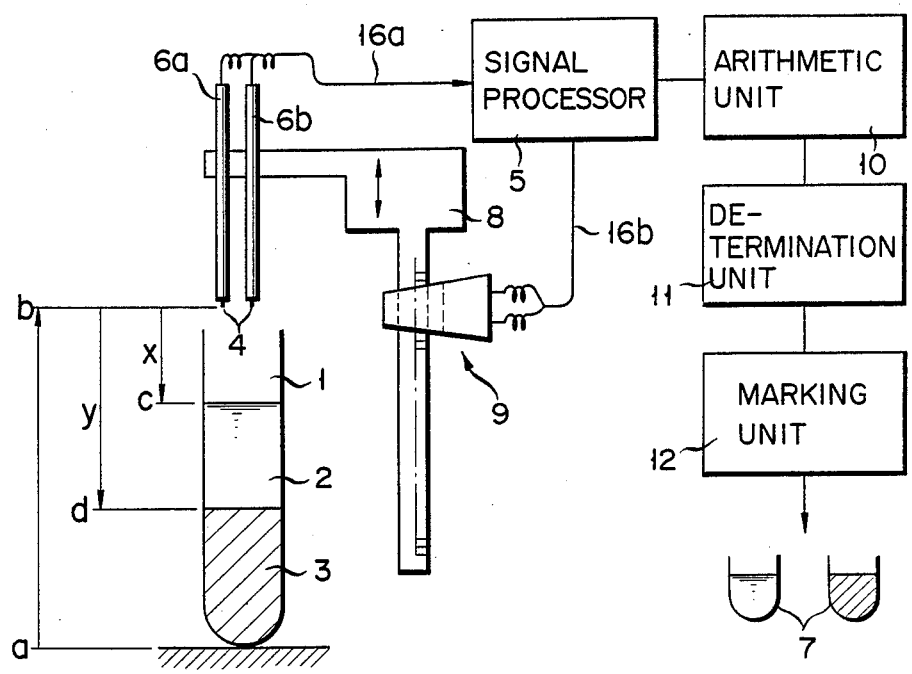
F I G. 1
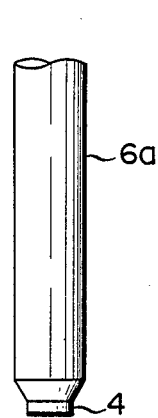
F I G. 3A
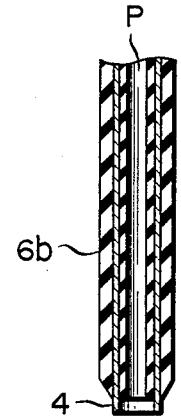
F I G. 3B

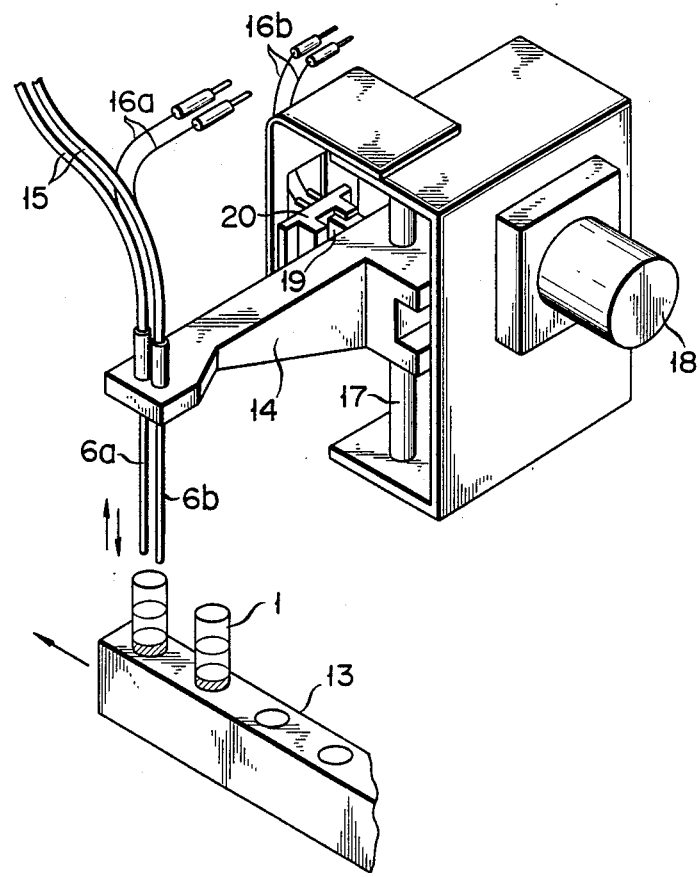
F I G. 2

METHOD OF PERFORMING MEASUREMENT OF HEMATOCRIT VALUE AND SEPARATE SAMPLING OF BLOOD COMPONENT

BACKGROUND OF THE INVENTION

1. Field of the Invention

The present invention relates to a method of measuring a hematocrit value of the blood, and separately sampling the plasma (or serum) and the blood cells (or blood clots), after separating blood into plasma and blood cells.

2. Description of the Related Art

The hematocrit value (to be referred to as an Ht value hereinafter) means a volume ratio of a blood cell component in blood. In general, the Ht value is represented by a ratio of a height of a settled blood cell component with respect to a total height of blood in a glass tube in which blood added with an anticoagulant is separated into a plasma component and a blood cell component. This value is an effective scale for checking whether blood is normal. Therefore, the Ht value is not only effective data for checking a human health condition but also essential data for checking whether blood is transfusable to patients. For this reason, Ht value measurement of blood from a donor is always performed upon blood transfusion. Separated plasma and blood cell components are sampled from a blood sample subjected to the Ht value measurement and used in various pathologic and compatibility tests.

The Ht value must be measured to assure safety of both a blood donor and a blood acceptor. For example, if the Ht value of a donor's blood is lower than a predetermined level, blood collection may cause anemia. Therefore, if the Ht value is significantly low, blood collection must be avoided. On the other hand, if the Ht value is abnormally high or low, an influence on a blood acceptor cannot be also neglected. Therefore, any use of such blood must be made very carefully or avoided in some cases.

The following methods and apparatus for measuring an Ht value and separately sampling a plasma component have been conventionally known.

An Ht measuring method is disclosed in Japanese Patent Disclosure (Kokai) No. 60-93348. In this method, blood added with an anticoagulant is centrifugally separated in a glass capillary and irradiated with collimated light, and the amount of light transmitted through the capillary is measured by a plurality of light-receiving elements. A transmitted light amount at a plasma portion is naturally larger than that at a blood cell portion. Therefore, the lengths of the plasma and blood cell portions are determined in accordance with a transmitted light amount detected by each light-receiving element, and the Ht value is calculated on the basis of the determined lengths and output to a suitable display unit such as a printer.

An apparatus for sampling a serum component is disclosed in Japanese Patent Disclosure (Kokai) No. 62-269037. By using this apparatus, serum can be separately sampled in an efficient manner from blood having a known Ht value as follows. That is, blood is separated into serum and blood clots in a collection tube. A suction nozzle located at a predetermined height from the bottom surface of the blood collection tube is gradually descended at a predetermined rate. When the distal end of the suction nozzle reaches the surface of the serum layer, the serum is sucked from the suction nozzle and flowed through a duct connected to the nozzle. The duct includes a detection electrode. When the electrode detects a flow of the serum, it is determined that the suction nozzle reaches the serum surface. Therefore, by calculating a descent distance in accordance with a descent rate of the nozzle and a time interval from a timing at which the suction nozzle starts descent to a timing at which a detection signal is obtained, the height of the serum surface can be obtained. By multiplying the height of the serum surface by the known Ht value, the bottom surface height of a serum layer can be obtained. As a result, a descent distance of the suction nozzle can be determined, and the serum can be separately sampled efficiently.

The above conventional techniques have the following drawbacks.

That is, in both of the above conventional techniques, only either Ht value measurement or serum sampling can be performed. Therefore, since Ht measurement and serum sampling must be independently performed, a considerably long time is required.

SUMMARY OF THE INVENTION

It is a first object of the present invention to provide a method capable of simultaneously performing Ht value measurement of a blood sample which is separated into two blood components in a predetermined vessel, and of sampling each blood component.

It is a second object of the present invention to provide a method capable of easily discriminating each blood component sampled from blood which has an abnormal Ht value.

Note that in this specification, the term "blood component" is taken to mean plasma (or serum) and blood cells (or blood clots) separated in a sample vessel by centrifugal separation or the like. In addition, a first component means the plasma (or serum) separated as a supernatant liquid of the two components, and a second component means the blood cells (or blood clots) settled downward.

The above first object of the present invention is achieved by a method of performing measurement of a hematocrit value and separate sampling of blood components, comprising the steps of:

lowering a probe from a predetermined initial height into a predetermined sample vessel containing a blood sample separated into a first component layer as an upper layer and a second component layer as a lower layer, the probe being integrally formed with a liquid surface detection electrode and a suction nozzle;

monitoring a descent distance upon descent of the probe;

generating a first liquid surface detection signal from the liquid surface detection electrode when a distal end of the probe reaches a liquid surface of the first component layer;

sampling a predetermined amount of the first component into separate sampling vessel means through the suction nozzle of the probe in response to the first liquid surface detection signal;

generating a second liquid surface detection signal from the liquid surface detection electrode when the distal end of the probe reaches a liquid surface of the second component layer;

sampling a predetermined amount of the second component into the separate sampling vessel means through the suction nozzle of the probe in response to the second liquid surface detection signal;

calculating liquid surface heights of the first and second component layers on the basis of the initial height of the probe, the monitored descent distance of the probe, and the first and second liquid surface detection signals; and calculating a total volume of the blood sample and a volume of the second component on the basis of the liquid surface heights of the first and second component layers, and calculating a hematocrit value from the volumes.

Preferably, the method of the present invention further comprises the step of:

comparing the calculated hematocrit value with a normal hematocrit value to check whether the sample blood is normal.

More preferably, the method of the present invention further comprises the step of:

applying an identification mark on one of the separate sampling vessel means or the sample vessel when the blood sample is determined to be abnormal.

BRIEF DESCRIPTION OF THE DRAWINGS

FIG. 1 is a schematic view showing an overall arrangement of an apparatus for carrying out a method of the present invention;

FIG. 2 is a perspective view showing a detection electrode and a drive unit of a suction/discharging means of the apparatus shown in FIG. 1;

FIG. 3A is a enlarged view showing one probe of the apparatus shown in FIG. 1; and FIG. 3B is a sectional view showing another probe and the detection electrode of the apparatus shown in FIG. 1.

DETAILED DESCRIPTION OF THE PREFERRED EMBODIMENT

FIG. 1 is a schematic view showing an overall apparatus used for carrying out a method of the present invention, and FIG. 2 is a perspective view showing a main part of the apparatus. Referring to FIG. 1, reference numeral 1 denotes a sample vessel having a predetermined size and shape. The sample vessel 1 contains a blood sample added with an anticoagulant. The blood sample is separated into plasma 2 and blood cells 3 by centrifugal separation. As shown in FIG. 2, the vessel 1 is housed in a cassette 13 and held at a predetermined height. The cassette 13 is conveyed by a conveyor means (not shown) in an arrow direction at a predetermined pitch.

Two probes 6a and 6b are arranged parallel to each other above the vessel 1. The probes 6a and 6b descend to enter into the vessel 1 and are fixed to a drive unit 8. The drive unit 8 can vertically move. Especially upon measurement, the unit 8 descends at a predetermined rate to move the probes 6a and 6b downward at a predetermined rate. Detection electrodes 4 extend from lower ends of the probes 6a and 6b, respectively. When the probes 6a and 6b descend, the electrodes 4 are brought into contact with the surfaces of the blood components 2 and 3 and detect the surfaces. An initial height of each probe is set at a level separated upward from a bottom surface level a of the vessel 1 by a distance b.

FIG. 2 shows an arrangement of the drive unit 8 in detail. That is, the unit 8 comprises an arm 14 for fixing the probes 6a and 6b, a guide 17 for supporting the arm 14 so that the arm 14 can vertically slide, and a motor 18 for vertically sliding the arm 14 along the guide 17. The motor 18 is connected to a control means (not shown) for controlling descent of the arm 14.

FIG. 3A shows an enlarged view of the probe 6a, and FIG. 3B shows an enlarged sectional view of the probe 6b. As is apparent from FIG. 3A and B, each of the probes 6a and 6b comprises an insulative cylindrical member having a path P therein. Each detection electrode 4 comprises a cylindrical member consisting of a conductive metal. The electrode 4 is embedded in the cylindrical probe 6a (6b) throughout its entire length and projects from its distal end by a predetermined length. When the probes 6a and 6b descend and the electrodes 4 are brought into contact with the liquid surface of the plasma layer 2 or the blood cell layer 3, an impedance or the like changes between the electrodes 4, thereby detecting the liquid surface.

As shown in FIG. 2, tubes 15 are connected to proximal end portions of the probes 6a and 6b, respectively. Each tube 15 is connected to a suction means (not shown). Predetermined amounts of the plasma 2 and the blood cells 3 in the sample vessel 1 are drawn by the suction means through the paths P in the probes 6a and 6b and injected in separate sampling vessels 7 as shown in FIG. 1. Lead wires 16a are connected to the electrodes 4 at the proximal end portions of the probes 6a and 6b, respectively. The lead wires 16a are connected to a signal processor 5. With this arrangement, liquid surface detection signals ar output from the detection electrodes 4 to the signal processor 5.

A distance detector 9 is disposed at the drive unit 8 (FIG. 1) and detects a moving distance of the unit 8 (i.e., a moving distance of the probes 6a and 6b). The detector 9 is connected to the processor 5 through lead wires 16b. FIG. 2 shows an arrangement of the detector 9 in detail. Referring to FIG. 2, the detector 9 includes a slit member 19 projecting from the side surface of the arm 14 and descending together with the arm 14. A large number of slits are formed in the slit member 19 at predetermined intervals. A photoelectric detector 20 is arranged to sandwich the slit member 19. The detector 20 is fixed to a housing and therefore does not move even when the arm 14 descends. A light source of the detector 20 is located at a portion extending above one side surface of the slit member 19. A light-receiving element for the light source is located at a portion extending above the other side surface of the slit member 19 so as to oppose the light source. Therefore, when the arm 14 descends, the slit member 19 descends between these portions of the detector 20, and the light-receiving element detects light from the light source each time a slit of the member 19 passes through a detection portion. Since the slits are formed at predetermined intervals, the number of detection times corresponds to a descent distance of the arm 14.

On the basis of a descent distance signal supplied from the distance detector 9 and liquid surface detection signals supplied from the detection electrodes 4, the signal processor 5 calculates descent distances x and y required for electrodes 4 to detect the liquid surfaces of the plasma 2 and the blood cells 3, respectively. The signals x and y are output from the processor 5 to an arithmetic unit 10.

The arithmetic unit 10 calculates liquid surface heights $c = b - x$ and $d = b - y$ of the plasma and blood cell layers 2 and 3, respectively, in accordance with the signals x and y and the initial height b of the electrodes 4. In addition, the unit 10 calculates a volume ($V_1$) of the sample vessel 1 corresponding to the liquid surface height c and a volume ($V_2$) thereof corresponding to the liquid surface height d, thereby calculating an Ht value from $V_2/V_1$.

The Ht value calculated as described above is output from the arithmetic unit 10 to a determination unit 11. The unit 11 stores normal Ht value ranges of male and female subjects. The unit 11 checks whether the Ht value supplied from the arithmetic unit 10 falls within the normal range. The unit 11 is connected to a marking unit 12 and outputs a determination result thereto.

The marking unit 12 comprises a marking means (not shown). In response to the signal from the determination unit 11, the marking means marks a predetermined number, symbol or the like on the separate sampling vessels 7 in which the blood component in the sample vessel 1 is injected.

An embodiment of the present invention using the above apparatus will be described below.

The cassette 13 is conveyed by the conveyor means (not shown) so that the sample vessel is stopped immediately below the probes 6a and 6b. Descent or lowering of the drive unit 8 is then started. That is, upon driving of the motor 18, the arm 14 descends along the guide 17.

At the same time, the distance detector 9 starts output of signals corresponding to descent distances of the drive unit 8. That is, since the slit member 19 descends together with the arm 14, the photoelectric detector 20 generates a distance signal pulse each time a slit of the member 19 passes through the detection portion. The signal pulses are supplied to the signal processor 5 through the lead wires 16b.

As the drive unit 8 descends as described above, the probes 6a and 6b descend at a rate equal to that of the unit 8 and enter into the sample vessel 1. When the distal ends of the probes 6a and 6b are brought into contact with the liquid surface of the plasma layer 2, the two detection electrodes 4 detect this. The descent of the drive unit 8 is stopped immediately after this liquid surface detection, and the distal ends of the probes 6a and 6b are held at a predetermined depth in the layer 2. The suction means (not shown) is activated by liquid surface detection signals. As a result, a predetermined amount of the plasma 2 is drawn by suction and injected into a corresponding one of the separate sampling vessels 7 through the probe 6a.

The liquid surface detection signals from the electrodes 4 are also supplied to the signal processor 5 through the lead wires 16a. As described above, processor 5 calculates the descent distance x required for the electrodes 4 to reach the liquid surface of the plasma layer 2. On the basis of the distance x, the arithmetic unit 10 calculates the liquid surface height $c=b-x$ of the layer 2 as described above. In addition, the unit 10 calculates the total volume $V_1$ of the blood sample (a volume from the bottom surface level a to the liquid surface height c of the vessel 1).

The motor 18 is then reactivated, and the drive unit 8 restarts descent. As the probes 6a and 6b further descend, the electrodes 4 are brought into contact with the liquid surface of the blood cell layer 3 and generate liquid surface detection signals. Upon generation of these detection signals, a predetermined amount of the blood cells 3 are drawn by suction. At this time, however, the blood cells 3 are drawn by suction through the other probe 6b not used for suction of the plasma 2 and injected in the other one of the separate sampling vessels 7 which does contain not the plasma 2.

The signal processor 5 calculates the descent distance y required for the electrodes 4 to reach the liquid surface of the layer 3. On the basis of the distance y, the arithmetic unit 10 calculates the liquid surface height $d=b-y$ of the layer 3. The unit 10 also calculates the volume $V_2$ of the blood cells 3 (a volume from the bottom surface level a to the liquid surface height d of the vessel 1).

The arithmetic unit 10 then calculates the Ht value of the blood sample on the basis of $Ht = V_2/V_1$. The determination unit 11 compares the calculated Ht value supplied from the unit 10 with the normal Ht value range. If the calculated value falls within the normal range, the next blood sample is measured. If the calculated value is determined to be abnormal, however, the marking unit 12 operates before measurement of the next sample. As a result, a predetermined symbol, number or the like is marked on the one of the separate sampling vessels 7 containing the blood component determined to be abnormal.

As is apparent from the above embodiment, according to the method of the present invention, upon one descent ration of the probes 6a and 6b into the sample vessel 1, separate sampling of plasma and blood cell components and measurement of an Ht value can be simultaneously performed. In addition, determination of normality of a blood sample can be performed on the basis of the measured Ht value. Also, in the above embodiment, when a blood sample is determined to be abnormal, marking means marks a symbol or the like on a separate sampling vessel in which a plasma or blood cells are injected from the sample. In this manner, normality of the separately sampled component can be easily checked. Furthermore, as is apparent from the above description, the method of the present invention can be carried out by using a relatively simple apparatus.

In the above embodiment, marking is performed for the separate sampling vessels 7 when the Ht value is abnormal. Marking, however, may be performed for the sample vessel 1.

In addition, each of the probes 6a and 6b may be obtained by coating an insulating film on a predetermined portion of the electrode 4 when formed into a probe-like shape.

What is claimed is:

1. A method of performing measurement of a hematocrit value and separate sampling of first and second blood components, comprising the steps of:

lowering a probe from a predetermined initial height into a predetermined sample vessel containing a blood sample separated into a first component layer as an upper layer and a second component layer as a lower layer, the probe being integrally formed with a liquid surface detection electrode and a suction nozzle;

monitoring a descent distance upon descent of said probe;

generating a first liquid surface detection signal from said liquid surface detection electrode when a distal end of said probe reaches a liquid surface of the first component layer;

sampling a predetermined amount of the first component into separate sampling vessel means through said suction nozzle of said probe in response to the first liquid surface detection signal;

generating a second liquid surface detection signal from said liquid surface detection electrode when the distal end of said probe reaches a liquid surface of the second component layer;

sampling a predetermined amount of the second component into the separate sampling vessel means through said suction nozzle of said probe in response to the second liquid surface detection signal;

calculating liquid surface heights of the first and second component layers on the basis of the initial height of said probe, the monitored descent distance of said probe, and the first and second liquid surface detection signals; and calculating a total volume of the blood sample and a volume of the second component on the basis of the liquid surface heights of the first and second component layers, and calculating a hematocrit value from the volumes.

2. A method according to claim 1, further comprising the step of:

comparing the calculated hematocrit value with a normal hematocrit value to check whether the sample blood is normal.

3. A method according to claim 2, further comprising the step of:

applying an identification mark on said separate sampling vessel means when the blood sample is determined to be abnormal.

4. A method according to claim 2, comprising the step of:

applying an identification mark on said sample vessel when the blood sample is determined to be abnormal.

5. A method according to claim 1, comprising:

forming said probe with a pair of liquid surface detection electrodes with a corresponding pair of suction nozzles.

6. A method according to claim 5, comprising:

sampling said first component through one of said pair of suction nozzles; and sampling said second component through the other one of said pair of suction nozzles.

7. A method according to claim 6, comprising:

arranging the separate sampling vessel means in the form of two separate sampling vessels;

injecting the sampled first component into one of said sampling vessels; and injecting the sampled second component into the other one of said sampling vessels.

* * * * *